United States Patent [19]

Nakamura et al.

[11] 4,225,675
[45] Sep. 30, 1980

[54] ADSORBENT FOR UROKINASE AND PROCESS FOR THE PRODUCTION OF UROKINASE

[75] Inventors: Hiroaki Nakamura, Kawasaki; Izumi Kumita, Ohiso; Yoshiji Sugita, Hiratsuka; Hideo Takagi, Ohiso, all of Japan

[73] Assignee: Nippon Soda Company, Ltd., Tokyo, Japan

[21] Appl. No.: 866,794

[22] Filed: Jan. 3, 1978

[30] Foreign Application Priority Data

Jan. 14, 1977 [JP] Japan .................................. 52/2327
Jan. 31, 1977 [JP] Japan .................................. 52/9450

[51] Int. Cl.² .................................................. C07G 7/026
[52] U.S. Cl. ........................................ 435/215; 435/815; 536/1
[58] Field of Search ........................... 195/66 B, 66 R; 435/215

[56] References Cited

U.S. PATENT DOCUMENTS 3,746,622  7/1973  Nishikawa et al. ............. 195/66 R
4,066,506  1/1978  Johnson et al. ................. 195/66 B

OTHER PUBLICATIONS

Holmberg et al, Biochimica and Biophysica Acta, vol. 445, No. 1, pp. 215-222, (1976).

*Primary Examiner*—Lionel M. Shapiro
*Attorney, Agent, or Firm*—George B. Oujevolk

[57] ABSTRACT

Highly pure urokinase can be produced by affinity chromatography on the adsorbent. The adsorbent comprises water insoluble carrier to which the group of the general formula

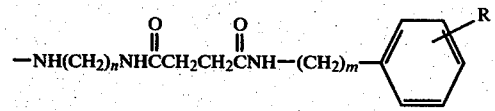

wherein
n is an integer of 5 to 12,
m is zero or one, and
R is (m- or p-) guanidino or (m- or p-) amidino group; is bound.

6 Claims, No Drawings

ADSORBENT FOR UROKINASE AND PROCESS FOR THE PRODUCTION OF UROKINASE

BACKGROUND OF THE INVENTION

This invention relates to the adsorbent for urokinase and the production of highly pure urokinase from human urine by affinity chromatography on the adsorbent.

Urokinase is a plasminogen-activating enzyme found in trace amount in human urine and is used as an effective thrombolytic agent and a drug used together with anticancer. High purity of urokinase is required because these drugs are used by an intravenous injection.

Recently, affinity chromatography began to be used as a method for the purification of human urokinase. For example, the method using basic amino acid, i.e. lysine, arginine, as a ligand [Japanese Patent Publication No. 441953/1976, Japanese Patent Publication No. 20596/1976, Japanese Patent Publication (Kokai Koho) No. 95183/1976, Japanese Patent Publication No. (Kokai Koho) 35481–35483/1976], and the method using an urokinase inhibitor contained in the tissue of the placenta as a ligand [Japanese Patent Publication No. 205977/1976] are known. It is, however, difficult to obtain a large amount of those materials used as a ligand in those methods. Furthermore, those affinity materials have not enough affinity to adsorb urokinase specifically from urokinase solution and the washing solution must be low in the concentration of salt contained therein when washing the affinity column before the elution of urokinase therefrom, which means that it is difficult to accomplish satisfactory purification of urokinase by those known methods.

Further, an adsorbent for urokinase similar to the adsorbent of the invention is known (Lass Holmberg et al., Biochimica et Biophysica Acta 445, 215, 1976). In the adsorbent, p-aminobenzamidine is coupled to agarose through a 6-carbon spacer. However, also these adsorbents have not enough affinity to urokinase in a condition of high salt concentration, therefore, using a high salt concentration of crude urokinase as a raw material causes leakage of urokinase and a high salt concentration of washing solution can not be used to attain efficient purification of urokinase.

SUMMARY OF THE INVENTION

It is an object of the invention to provide an improved adsorbent for urokinase and a process for the production of urokinase by affinity chromatography using said adsorbent.

The inventors found that the materials using the compound of the general formula [I]

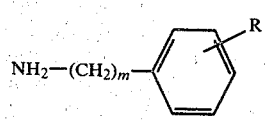

wherein
m is zero or one, and R is (m- or p-) guanidino or (m- or p-) amidino group, as a ligand have a property to adsorb urokinase specifically. The ligand is bound to a water insoluble carrier such as agarose through diaminoalkane and succinic anhydride. The group which is bound to the water insoluble carrier can be shown as follows:

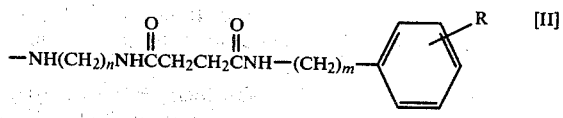

wherein
n is an integer of 5 to 12,
m is zero or one, and
R is (m- or p-) guanidino or (m- or p-) amidino group.

Highly pure urokinase can be produced from human urine by affinity chromatography on the above-mentioned adsorbent in a good yield. Because of the high affinity of the adsorbent to urokinase, a considerably high salt concentration of washing solution can be used after the adsorption of urokinase. Consequently, the washing is very efficient and highly pure urokinase can be easily obtained. Also because of the high affinity, even fresh human urine may be contacted with the adsorbent in order to adsorb urokinase. Another advantage of the invention is that the adsorption of urokinase can be attained sufficiently in the neutral or alkaline solution in this invention, which means high recovery of urokinase by this invention because human urine contains uropepsin which is active in acidic solution and urokinase is apt to be inactivated with the uropepsin in acidic condition.

Other and further objects, features and advantages of the invention will appear more fully from the following description.

DETAILED DESCRIPTION OF THE INVENTION

The adsorbent of the invention is the material wherein the guanidine or amidine derivatives indicated by the formula [I] is bound to a water insoluble carrier through a spacer. More particularly, the adsorbent is the water insoluble material such as agarose having the group of the formula [II]. As the water insoluble carrier, any material having the functional group to which the terminal amino group of the spacer can be coupled may be used. Suitable carriers are polysaccharides such as agarose, crosslinked dextran, celluloses and agar-agars, polymer such as acrylamide, and glass powder. Agarose is most preferable carrier. Agarose or modified agarose, for example, agarose to which hexamethylenediamine is coupled, is sold on the market as a carrier for affinity chromatography. Those products on the market can be used in this invention.

The adsorbent of the invention can be constructed by the known process. For example, in the case that the carrier is agarose, first, the agarose is activated with cyanogen bromide and sequently coupled to diaminoalkane and then succinic anhydride. The affinity ligand precurser, the compound of formula [I], is then coupled to the modified agarose in the presence of water soluble carbodiimides to form the adsorbent of the invention.

In the case that the carrier is carboxymethylcellulose, it is coupled to diaminoalkanes by the reaction in the presence of water soluble carbodiimides. Then the adsorbent is constructed as same as above. Similar method is disclosed in the literature, "Method in Enzymology 34 451-455 (1974)".

In the case of the ligand being guanidino derivatives, the spacer may be ε-aminocaproic acid or ω-aminohepanoic acid as well as the one indicated by the formula [II], while in the case of the ligand being amidine derivatives, the spacer is necessarily the one indicated by the formula [II] in order to maintain the property of the adsorbent which adsorbs urokinase specifically.

In the formula [I], the substituent R is preferably m-guanidino or m-amidino group, n is preferably 6 and m is preferably 0.

When carrying out the process of this invention, human urine or pre-treated human urine is applied to the column packed with the adsorbent of the invention. The adsorbed urokinase is eluted with a pertinent eluting solution after washing the column sufficiently to remove impurities.

Though the pH value is not critical to adsorb urokinase specifically, the neutral or alkaline condition is preferable. Usually, an impure aqueous solution of crude urokinase is prepared so as to make a salt concentration of the solution between 0.2 and 2 M, the pH of the solution is adjusted to pH 5.5–10, preferably 5.5–10 with a pertinent buffer solution, and then the solution is contacted with the adsorbent. The washing solution is an aqueous solution of inorganic salt such as sodium chloride. The concentration of the inorganic salt is in the range of from 0.2 to 1.5 M, preferably from 0.3 to 0.5 M. The eluting solution may be water or aqueous solution of inorganic salt such as sodium chloride, ammonium sulfate, adjusted pH value to 3.5–5.5, preferably 4–5, or a high concentration of aqueous solution of urea. Suitable eluting solution is water or the aqueous solution of sodium chloride adjusted to the above pH with a pertinent buffer solution such as acetate buffer, the concentration of sodium chloride usually being the same as that of the washing solution or lower than that. It is preferably 0.5 M or lower, more preferably 0.3 M or lower. Highly pure urokinase is obtained from the eluate in the usual method, namely by lyophilization after desalting.

Because of high affinity of the adsorbent to urokinase, even fresh human urine may be applied to the adsorbent, however, human urine is usually pretreated in a usual method before it is applied to the affinity column. For example, the foam made by stirring human urine is collected and a defoaming agent is added thereto and the solution is adjusted to pH 8.5–9 to form precipitates. The resulting supernatant solution may be applied to the affinity column. Further, the supernatant solution may be treated, namely, a weakly acidified supernatant solution is contacted with diatomaceous earth such as cerite to recover the crude urokinase in a usual method. The crude urokinase is dissolved in water and the resulting solution may be applied to the affinity column of this invention.

Further, the inventors have accomplished more preferable process in order to produce highly pure urokinase efficiently. In other words, the solution containing crude urokinase which is prepared as mentioned above is purified by hydrophobic chloromatography on a protein adsorbent and the partially purified urokinase solution is applied to the affinity column of the invention.

Recently, hydrophobic chromatography wherein the interaction between hydrophobic region of protein and hydrophobic group such as long chain of methylene and aromatic ring is utilized, is being watched as a means for the purification of enzyme by fractionation.

The protein adsorbent for the hydrophobic chromatography is the material which comprises an water insoluble carrier such as agarose and the compounds indicated by the formula [III]:

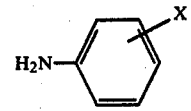

[III]

wherein X is hydrogene, halogene, alkyl group or alkoxycarbony group.

The compound of the formula [III] is coupled to the carrier directly or through spacers. Usually, spacer is first coupled to the carrier, namely, the group of the formula [IV] or [V]

$$-NH(CH_2)_l NHCOCH_2CH_2COOH \quad [IV]$$

$$-NH(CH_2)_l COOH \quad [V]$$

in which l is an integer of from 3 to 10, is bound to the carrier. The compound of the formula [III] is coupled to the modified carrier. Thes protein adsorbents are constructed in a usual method similarly to the adsorbent for urokinase of this invention. The carrier may be the same one as used in the adsorbent for urokinase.

When carrying out the hydrophobic chromatography, the solution containing the crude urokinase which is prepared from human urine in a usual simple method as mentioned above, is adjusted to the salt concentration of 0.2 to 2 M, preferably 0.2 to 1 M. The solution is then made to flow through the hydrophobic column. Proteins having higher affinity to the protein adsorbent than urokinase is removed by the adsorption. The effluent is then applied to the affinity column of the invention. The pH is not critical when carring out the hydrophobic chromatography, however, the pH is usually adjusted to pH 5.5–10, preferably 6–8.5 at which pH urokinase is stable against inactivation.

The above method combining the affinity chromatography with hydrophobic chromatography is very advantageous for producing highly pure urokinase. In this combination the order of sequence may be reversed, it is, however, preferable in the industrious process to apply the effluent of hydrophobic chromatography to the affinity chromatography.

To further illustrate this invention, and not by way of limitation, the following examples are given.

Pre-treatment of human urine:

Fresh human urine was stirred and the resulting foam was separated. A defoaming agent was added to the foam and adjusted to pH 8.7 by adding aqueous NaOH. The resulting precipitate was removed to obtain the supernatant solution containing crude urokinase. The supernatant solution is hereinafter called "crude urokinase solution A". After adjusting the crude urokinase solution A to pH 5.5 by adding aqueous HCl, it was contacted with diatomaceous earth to adsorb urokinase. The adsorbed urokinase was eluted with 3% aqueous solution of $NH_3$ after washing the diatomaceous earth with water to remove impurities. The eluate was ultrafiltrated by follow-fiber and lyophilized to obtain the powder of crude urokinase. The powder of the crude urokinase is hereinafter called "crude urokinase B".

EXAMPLE 1.

To a suspension of 20 ml AH-Sepharose (product by Farmacia·Fine Chemicals) in 20 ml of water were added 2 g of succinic anhydride and the reaction was allowed to proceed at 4° C., maintaining the pH at 6 by adding aqueous NaOH. After the change of the pH disappeared, the reaction was further continued for 5 hours. The reaction mixture was filtered and washed with 1 l of water to obtain the modified Sepharose, succinyl AH-Sepharose. To a suspension of the resulting succinyl AH-Sepharose in 50 ml of 40% aqueous solution of dimethyl formamide were added 470 mg of m-aminophenylguanidine HCl and the pH was adjusted to 4.8. To the mixture were added 1.23 g of 1-ethyl-3-(3-dimethyl-aminopropyl)-carbodiimide dissolved in 2 ml of water and the reaction was allowed to proceed at room temperature for 18 hours. During the first one hour of the reaction the pH was maintained at 4.8 by adding 1 N HCl. The reaction mixture was filtered and washed with 500 ml of 0.5 M NaCl and then 500 ml of distilled water to obtain the adsorbent for urokinase.

Through the column packed with 20 ml of the adsorbent for urokinase made as above were passed 4 l of crude urokinase solution A adjusted to pH 7.5 to adsorb urokinase.

The column was washed with 1 M NaCl and then the adsorbed urokinase was eluted with 6 M urea solution.

The fraction containing urokinase was desalted, concentrated and lyophilized in a usual way to obtain urokinase with a specific activity of 24,000 international units per 1 mg of protein in a 75% yield.

EXAMPLE 2.

An absorbent for urokinase was constructed in the same way as in Example 1, using p-aminobenzamidine HCl instead of m-aminophenylguanidine HCl. Through the column packed with this adsorbent was passed 5 ml of crude urokinase solution (50,000 international units of urokinase, specific activity of 21,000 international units/mg protein) which was prepared by dissolving the crude urokinase B in 0.1 M phosphate buffer (pH 7.5). The column was washed with 0.1 M NaCl solution to remove impurities and then the adsorbed urokinase was eluted with 0.5 M NaCl in 0.1 M acetate buffer (pH 4.0). The fraction containing urokinase was dialyzed and lyophilized in a usual way to obtain powder of urokinase with a specific activity of 48,000 international units/mg protein in a 85% yield.

EXAMPLE 3.

An adsorbent for urokinase was constructed in the same way as in Example 1, using m-aminobenzamidine HCl instead of m-aminophenylguanidine HCl.

10 l of human urine was concentrated by follow-fiber and adjusted to pH 8.5 by adding aqueous NH$_3$. The resulting precipitate was removed to obtain the clarified crude urokinase solution.

Through the column packed with the adsorbent was passed 300 ml of the crude urokinase solution adjusted to pH 7.5 to adsorb urokinase. The column was washed with 1.5 M NaCl and then the adsorbed urokinase was eluted with 0.5 M NaCl in 0.1 M acetate buffer (pH 4.0). The fraction containing urokinase was desalted and concentrated by Diaflofilter (product by Amicon Co.) and lyophilized to obtain 39,000 international units of urokinase powder with a specific activity of 32,000 international units/mg protein.

EXAMPLE 4.

To a suspension of 100 ml of Sepharose 4B (product by Pharmacia Fine Chemicals) in 100 ml of water were added 200 ml of 5% aqueous solution of CNBr with stirring. The reaction was allowed to proceed for 10 minutes at 20° C. while adding NaOH aqueous solution to keep the reaction mixture at pH 11. The reaction mixture was then filtered and the activated Sepharose was washed with 1.5 l of 0.1 M NaHCO$_3$. The activated Sepharose was rapidly suspended in the solution of ε-aminocaproic acid which was prepared by dissolving 1.31 g of ε-aminocaproic acid in 100 ml of 0.1 M NaHCO$_3$ and then adjusting to pH 9.5, and was reacted for 16 hours at 4° C. The reaction product was washed with 1 l of 0.5 M NaCl and then 1 l of distilled water to obtain the modified Sepharose, Sepharose-ε-aminocaproic acid. To this modified Sepharose were added the aniline solution which was prepared by dissolving 400 mg of aniline in 250 ml of 40% dimethyl formamide and adjusting to pH 4.7. To the mixture were added 3 g of 1-ethyl-3-(3-dimethylaminopropyl)carbodiimide HCl dissolved in 5 ml of water and the reaction was allowed to proceed for 18 hours at the room temperature. During the first one hour of the reaction the pH was maintained at pH 4.8 by adding 1 N HCl. The reaction mixture was filtered and washed with 500 ml of 0.5 M NaCl and then 500 ml of distilled water to obtain protein adsorbent for hydrophobic chromatography.

The column of 2.5 cm diameter packed with this protein adsorbent was connected with another column of 2.5 cm diameter packed with 100 ml of the adsorbent for urokinase mentioned in Example 2 in series. Through the hydrophobic column was passed a crude urokinase solution containing 10 million international units of urokinase which was prepared by dissolving the crude urokinase B in 500 ml of 0.2 M NaCl in 0.1 M phosphate buffer (pH 7.4). The hydrophobic column was washed with 2 l of 0.2 M NaCl in 0.1 M phosphate buffer (pH 7.4). The effluent from the hydrophobic column was successively passed through the affinity column. Then the hydrophobic column was removed and the urokinase adsorbed by the affinity column was eluted with 0.1 M acetate buffer (pH 5.0).

The fraction containing urokinase was ultrafiltrated, dialyzed and filtrated to obtain 8.56 million international units of urokinase with a specific activity of 82,700 international units/mg protein.

EXAMPLE 5.

A protein adsorbent for hydrophobic chromatography was constructed in the same way as in Example 4, using 500 mg of n-butyl-p-aminobenzoate instead of 400 mg of aniline.

A crude urokinase solution containing 10 million international units of urokinase, which was prepared by dissolving the crude urokinase B in 500 ml of 0.4 M NaCl in 0.1 M phosphate buffer (pH 7.0), was treated in the same way as in Example 4 except that the eluting solution was 0.1 M acetate buffer (pH 4.5) instead of 0.1 M acetate buffer (pH 5.0). Thus, 7.8 million international units of purified urokinase with a specific activity of 95,200 international units/mg protein was obtained.

Pyrogen tests were applied to the urokinase obtained in Examples 4 and 5 according to the Japanese pharmacopoeia. The results were negative at a dosage of 8,000 international units/p-kg.

In order to compare the adsorbent of the invention with the one disclosed in Biochimica et Biophysica Acta, 445, 215 (1976), the following comparative example is carried out:

COMPARATIVE EXAMPLE

A crude urokinase solution prepared as same as in Example 4, in which the specific activity of the urokinase was 3,000 international units/mg protein, was passed through the affinity column packed with an adsorbent of this invention or a known adsorbent. The used adsorbents were as follows:

(1) The adsorbent of the invention: the same one as in Example 2,

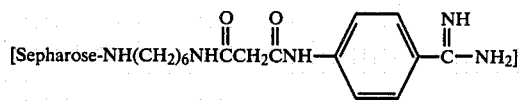

(2) The known adsorbent: the adsorbent in which p-aminobenzamidine is coupled to CH Sepharose (product by pharmacia Fine Chemicals),

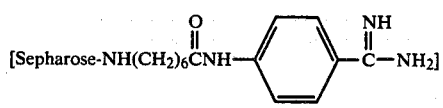

The each column adsorbing urokinase was successively washed with
(I) 0.15 M NaCl in 0.005 M phosphate buffer (pH 7.5),
(II) 0.4 M NaCl in 0.005 M phosphate buffer (pH 7.5),
(III) 0.8 M NaCl, and then
(IV) 0.4 M NaCl in 0.1 M acetate buffer (pH 4.0).

The amount of urokinase contained in each effluent was analyzed and the following results were obtained.

The amount of urokinase contained in each effluent (weight % per adsorbed urokinase)

| Adsorbent | Washing solution | | | |
|---|---|---|---|---|
| | (I) | (II) | (III) | (IV) |
| (1) | 0 | 0 | 0 | 85 (98,000)* |
| (2) | 7.5 | 12 | — | 68 (32,000)* |

*Specific activity (international units/mg protein) of the recovered urokinase

As shown above, in the case of adsorbent (2), about 20% of urokinase was eluted with 0.4 M NaCl, while in the case of adsorbent (1) of the invention, urokinase was not eluted even with 0.8 M NaCl, which means that sufficient washing can be attained to obtain highly pure urokinase in this invention.

We claim:

1. A process for the production of highly pure urokinase which comprises passing an impure aqueous solution of urokinase through a first column packed with a protein absorbent comprising a water insoluble carrier to which is bound a material selected from the group consisting of

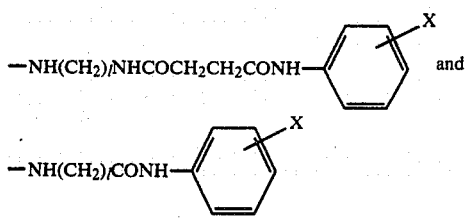

where l is an integer of from 3 to 10, and X is a material selected from the group consisting of hydrogen, alkyl, halogen and alkoxycarbonyl; and, passing the effluent therefrom through a second column packed with an adsorbent from urokinase comprising a water insoluble carrier to which is bound a material selected from ghe group of the general formula

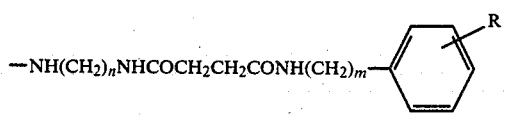

where
n is an integer of from 5 to 12,
m is 0 or 1, and
R is (m- or p-) guanidino or (m- or p-) amidino group,
and, eluting the adsorbed urokinase.

2. A process according to claim 1, wherein the protein adsorbent is a water insoluble carrier to which is bound a material selected from the group of the general formula

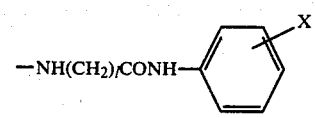

and X is hydrogen or lower alkoxycarbonyl.

3. A process according to claim 1, wherein the water insoluble carrier is agarose.

4. A process according to claim 1 wherein n is 6 and m is 0.

5. A process according to claim 2, wherein is 5, and X is butoxycarbonyl.

6. A process according to claim 1, wherein the impure aqueous solution of urokinase, the salt concentration of which is in a range of from 0.2 to 2 M, and the pH of which is in a range of from 5.5 to 10, is passed through a column packed with the protein adsorbent, and the effluent therefrom is passed through a column packed with the adsorbent for urokinase and then the adsorbed urokinase is eluted with water adjusted to a pH in a range of from 3.5 to 5.5 or an aqueous solution of 0.5 M or less inorganic salt adjusted to a pH in a range of from 3.5 to 5.5.

* * * * *